April 29, 1941. P. J. GOEBEL Plant Pat. 463
CARNATION PLANT
Filed May 31, 1940
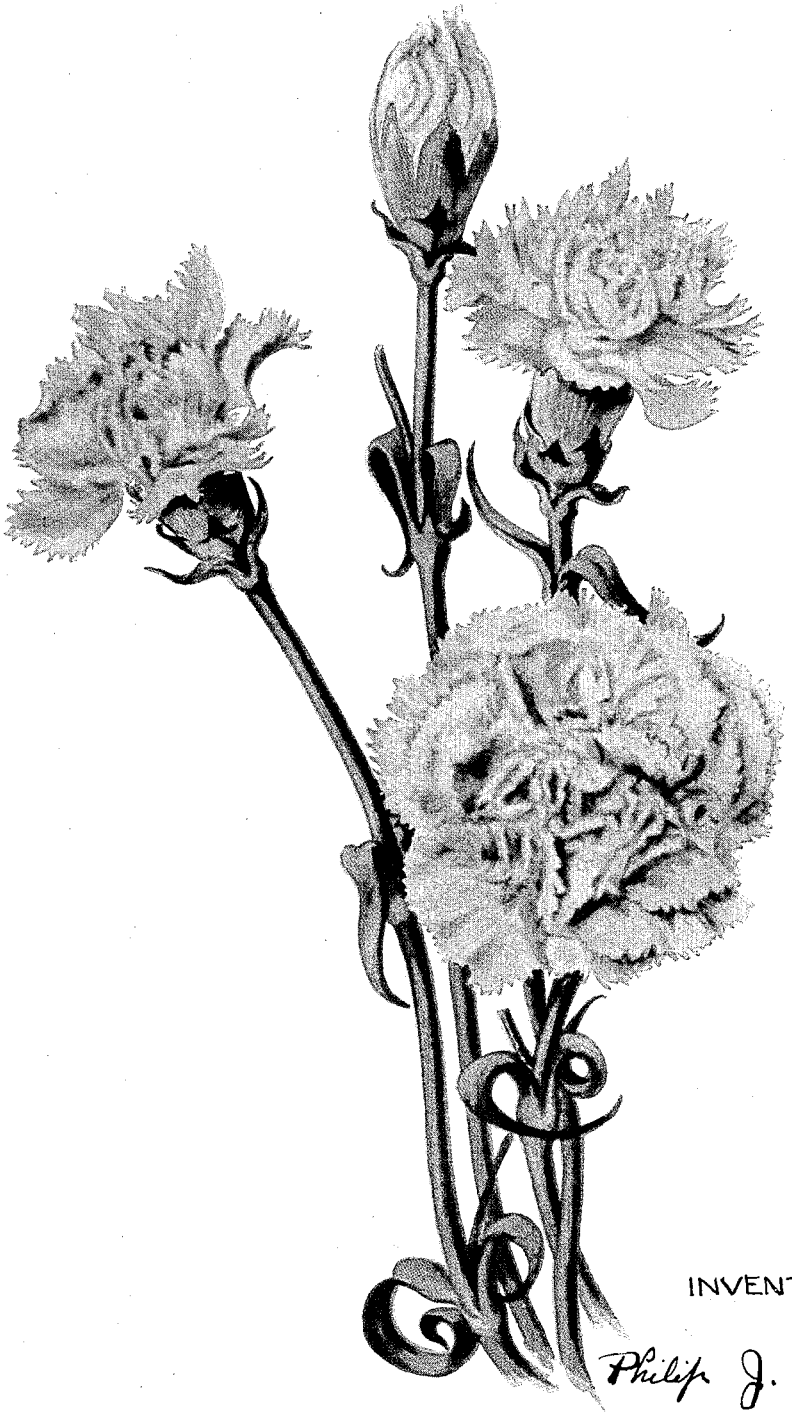
INVENTOR
Philip J. Goebel
By Orville M Kile
PLANT PATENT AGENT.

Patented Apr. 29, 1941

Plant Pat. 463

UNITED STATES PATENT OFFICE

463

CARNATION PLANT

Philip J. Goebel, Des Peres, Mo.

Application May 31, 1940, Serial No. 338,276

1 Claim. (Cl. 47—60)

My present discovery relates to improvements in red carnations of the large-flowered type known as forcing carnations. It is a sport of the variety King Cardinal which is the subject of Plant Patent No. 148, and is more like that variety than any other known to me.

While the differences between these two varieties may not be readily noticeable at a glance, examination will show a number of differences which are useful and desirable improvements over the parent variety.

The blossoms of my variety are somewhat larger than those of the parent variety and their color is darker and more brilliant and will hold under any weather conditions. A very noticeable difference is in the shape of the buds of the two varieties, the parent variety having long, slender buds while the new variety has buds which are thicker and more bulged, due no doubt to the greater number of petals inclosed in the new variety. Although the stems of the King Cardinal are notably strong and sturdy, the stems of my new variety are heavier and stiffer than those of its parent.

I discovered this new carnation as a sport branch of King Cardinal several years ago. I have since been propagating it by cuttings and its characteristics have proven to be permanently fixed.

The original paintings accompanying this application show in approximately true colors and slightly reduced size, one bud, two partly opened flowers, and a fully opened flower, together with stems and foliage.

Following is a detailed description of the new variety. Color plate references are to Ridgway's Color Standards and Nomenclature. Where no plate number is given, the ordinary dictionary term is intended.

*The plant*

Growth: Vigorous and upright, attaining a height of 3 or 4 feet.

Flowering habit: Very free flowering.

Foliage: Moderate in quantity; Dark Dull Yellow Green (Plate XXXII) to Empire Green (Plate XXXII), covered with gray bloom. Leaves medium width; upper pair curled only slightly, lower pairs more.

Stems: Very strong and stout; long and straight; same color as foliage; nodes relatively large.

*The flower*

Bud: Large; bulged or ball-shaped until after color shows. Color is a rich Scarlet (Plate I).

*Calyx.*—Broad, tough, strong and non-splitting; color ranges from Oil Green (Plate VI) at top to Cedar Green (Plate VI) at the base.

*Bracts.*—Strong, with tips much darker than calyx.

Blossom:

*Size.*—Very large. Averages 3½ to 3¾ inches in diameter although under the most favorable conditions it attains 4 inches or more. Compared with its parent grown under the same conditions, it usually runs about one-half inch larger.

*Petalage.*—In March the average number of petals is 47.

*Form.*—High-centered; full-petaled; regular.

*Color.*—Between Scarlet Red and Spectrum Red (Plate I). This color is very evenly distributed over the visible portions of the petals and is very brilliant, particularly in artificial light. It does not change or fade and the brilliance is retained throughout the life of the blossom. The petal shank or claw is greenish white.

*Fragrance.*—Very mild.

*Longevity.*—Excellent.

*Petals.*—*Shape*—obovate, with long shank. Irregularly serrated and notched. *Size*—outer petals 2½ inches long, including shank which is about half the length. Width at broadest point averages 1½ inches. *Aspect*—slightly velvety on upper surface. *Substance*—good. *Arrangement*—outer petals nearly flat and at right angles to stem. Inner petals crinkled and irregularly arranged.

Reproductive organs:

*Ovary.*—Large and high-set.

*Pistils.*—Pink; usually two in number; slightly curled at upper end; about 1½ inches long and seldom visible in the open flower.

*Stamens.*—White; few; ragged; usually lacking anthers; much shorter than pistils.

*Comparison*

The known variety which my variety most resembles is its parent, King Cardinal. My new variety differs from King Cardinal principally in the following points:

1. My new variety has stems that are heavier and stiffer than those of King Cardinal.

2. Buds are larger, shorter, thicker and more bulged.

3. Blossoms are about one-half inch larger in diameter and are higher centered.

4. Blossoms have 8 to 15 more petals. In March my variety averages about 47 petals as compared with 35 for King Cardinal at the same season and grown under the same conditions.

5. Color is slightly deeper in shade.

6. Color is more uniform and slightly more brilliant.

7. Color is not subject to streaking in cloudy weather, while King Cardinal sometimes streaks a little.

8. Color or brilliance does not change but is retained until blossom dies, while King Cardinal turns dark around the edges and fades slightly.

Having thus disclosed my invention, I claim:

A new and distinct variety of carnation plant substantially as shown and described, characterized particularly by its stout, heavy stems; its large, thick, bulging buds; and its very large full-petaled, high-centered blossoms having a uniform, brilliant Scarlet Red to Spectrum Red color which it retains regardless of weather conditions.

PHILIP J. GOEBEL.